US00PP25289P3

(12) United States Plant Patent
Klemm et al.

(10) Patent No.: US PP25,289 P3
(45) Date of Patent: Feb. 10, 2015

(54) *LOBELIA* PLANT NAMED 'KLELE12472'

(50) Latin Name: *Lobelia erinus*
Varietal Denomination: KLELE12472

(71) Applicant: Klemm+Sohn GmbH & Co. KG, Stuttgart (DE)

(72) Inventors: Nils Klemm, Stuttgart (DE); Guido Von Tubeuf, Stuttgart (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 154 days.

(21) Appl. No.: 13/573,956

(22) Filed: Oct. 16, 2012

(65) Prior Publication Data
US 2014/0109278 P1 Apr. 17, 2014

(51) Int. Cl.
*A01H 5/00* (2006.01)

(52) U.S. Cl.
USPC ..... Plt./451

(58) Field of Classification Search
CPC ..... A01H 5/02
USPC ..... Plt./451
See application file for complete search history.

*Primary Examiner* — June Hwu
(74) *Attorney, Agent, or Firm* — Jondle & Associates, P.C.

(57) ABSTRACT

A new and distinct *Lobelia* plant named 'KLELE12472' particularly distinguished by dark blue flowers with white eye and a medium compact, mounding growth habit, is disclosed.

1 Drawing Sheet

Genus and species: *Lobelia erinus*.
Variety denomination: 'KLELE12472'.

BACKGROUND OF THE NEW PLANT

The present invention comprises a new and distinct variety of *Lobelia*, botanically known as *Lobelia erinus*, and hereinafter referred to by the variety name 'KLELE12472'. The new variety resulted from a controlled cross conducted in June 2006 in Stuttgart, Germany, between female parent *Lobelia* plant named 'LE 06 0012' (unpatented) and male parent *Lobelia* plant named 'LE 06 0028' (unpatented). A single plant selection was subsequently chosen for further evaluation and asexual propagation.

The new variety was first propagated via vegetative cuttings and in vitro propagation in May 2007 in Stuttgart, Germany, and has been asexually reproduced repeatedly by vegetative cuttings for 15 generations. 'KLELE12472' has been found to retain its distinctive characteristics through successive asexual propagations via vegetative cuttings.

Plant Breeder's Rights for this variety were applied for in Canada on Feb. 17, 2012. 'KLELE12472' has not been made publicly available anywhere in the world more than one year prior to filing of this application.

SUMMARY OF THE INVENTION

The following are the most outstanding and distinguishing characteristics of this new variety when grown under normal horticultural practices in a glass greenhouse in Stuttgart, Germany.

1. Dark blue flowers with white eye; and
2. Medium compact, mounding growth habit.

DESCRIPTION OF PHOTOGRAPH

This new *Lobelia* plant is illustrated by the accompanying photograph which shows overall plant habit including blooms, buds, and foliage of the plant in full color. The colors shown are as true as can be reasonably obtained by conventional photographic procedures. The photograph was taken in spring of 2012 on a 3-month old *Lobelia* plant grown in a 10 centimeter pot in a glass greenhouse in Stuttgart, Germany under normal horticultural practices.

DESCRIPTION OF THE NEW VARIETY

The following detailed descriptions set forth the distinctive characteristics of 'KLELE12472'. The data which define these characteristics were collected from asexual reproductions carried out in Stuttgart, Germany. The plant history was taken in the spring of 2012 on 3-month old plants grown in 10 centimeter pots in a glass greenhouse with a pinch date at week eight. Color readings were taken under natural light. Color references are primarily to The R.H.S. Colour Chart of The Royal Horticultural Society of London (R.H.S.), Fifth Edition (2007).

DETAILED BOTANICAL DESCRIPTION OF THE NEW PLANT

Classification:
- *Botanical.*—*Lobelia erinus.*
- *Common name.*—*Lobelia.*
- *Designation.*—'KLELE12472'.

Parentage:
- *Female parent.*—*Lobelia* plant named 'LE 06 0012' (unpatented).
- *Male parent.*—*Lobelia* plant named 'LE 06 0028' (unpatented).

Growth:
- *Growth and branching habit.*—Mounding.
- *Form.*—Rounded to flat.
- *Height* (*measured from the top of the soil, including any flowers*).—15.0 cm.

*Width* (*horizontal plant diameter, including any flowers*).—12.0 cm.
*Time to produce a finished flowering plant.*—9 weeks.
*Outdoor plant performance*.—Very good.
*Time to initiate roots.*—3 weeks.
*Root description*.—Fine, white roots, freely branching and dense.

Leaves:
*Arrangement*.—Alternate.
*Length.*—2.0 cm to 2.5 cm.
*Width.*—0.3 cm to 0.4 cm.
*Shape*.—Elliptical.
*Margin*.—Serrate to lanceolate.
*Apex*.—Obtuse.
*Base*.—Acute.
*Texture* (*both upper and lower surfaces*).—Smooth.
*Color* (*immature and mature leaves*).—Upper surface: RHS 137A. Lower surface: RHS 137C.
*Venation*.—Pinnate.

Stems:
*Length.*—12.0 cm.
*Diameter.*—0.2 cm.
*Internode length.*—1.0 cm to 1.5 cm.
*Color*.—RHS 137B.
*Texture*.—Smooth.
*Stem anthocyanin*.—Absent.
*Peduncle*.—Color: RHS 137B. Length: 1.0 cm to 3.0 cm. Diameter: 0.05 cm. Texture: Smooth.

Flower buds:
*Color* (*when first opening*).—Upper surface: RHS 95B. Lower surface: RHS 193A.
*Shape*.—Inverse drop.
*Diameter.*—0.25 cm.
*Length.*—0.8 cm.

Inflorescence:
*Blooming habit*.—Continuous.
*Lastingness of individual blooms on plant*.—Approximately 1 week.
*Fragrance*.—Absent.
*Inflorescence type*.—Raceme.
*Quantity of flowers and buds per flowering branch.*—10 to 15.
*Average inflorescence size.*—20.0 cm.

Flowers:
*Arrangement*.—Flowers form at apical axils, one flower per axil.
*Flower diameter* (*horizontal*).—1.5 cm.
*Flower height* (*vertical*).—0.6 cm.
*Immature flower*.—Upper lobes color: Upper surface: Close to RHS N89A. Lower surface: RHS 95C on the outer region and RHS 97D on the central region. Lower lobes color: Upper surface: Close to RHS N89A. Lower surface: RHS 94A.
*Mature flower*.—Upper lobes: Color: Upper surface: Close to RHS N89A. Lower surface: RHS 95C on the outer region and RHS 97D on the central region. Length: 0.4 cm. Width: 0.15 cm. Shape: Obovate. Apex: Obtuse. Margin: Entire. Texture (both upper and lower surfaces): Smooth. Lower lobes: Color: Upper surface: Close to RHS N89A with white eye at base of more than RHS NN155D. Lower surface: RHS 94A. Length: 0.9 cm. Width: 0.6 cm. Shape: Obovate. Apex: Obtuse. Margin: Entire. Texture (both upper and lower surfaces): Smooth.
*Corolla*.—Color inside: Base color of more than RHS NN155D with stripes of RHS 95B and RHS 3A. Color outside: Close to RHS 94A; white with weak blue pattern Tube length: 0.7 cm. Diameter (at top of corolla tube): 0.2 cm.
*Calyx*.—Quantity of sepals: 5. Color: Upper surface: RHS 137A (fused part) and slight RHS 141C anthocyanin coloration near margins. Lower surface: RHS 137A with slight anthocyanin coloration near margins. Anthocyanin: Yellow dots between calyx and lower lob of RHS 3A. Length: 0.9 cm. Fused part: 0.4 cm. Non-fused part: 0.5 cm. Diameter (at fusion point): 0.1 cm. Shape: Funnel, star-shaped with fused sepals in lower half. Apex: Acute. Texture (both upper and lower surfaces): Smooth.

Reproductive organs:
*Androecium*.—Quantity of anthers: 5. Filament length: 0.7 cm. Filament color: RHS 95A at the apex; more than RHS NN155D at the base. Pollen color: Grey. Pollen amount: Medium.
*Gynoecium*.—Pistil length: 0.5 cm. Stigma color: RHS N187A. Style length: 0.6 cm. Style color: RHS 142B.

Fruit and seed set: None observed.
Disease and insect resistance: Typical of species.

COMPARISON WITH PARENTAL AND COMMERCIAL VARIETIES

'KLELE12472' differs from the female parent, 'LE 06 0012', (unpatented) in that 'KLELE12472' has dark blue flowers, whereas 'LE 06 0012' has medium blue flowers with a white eye.

'KLELE12472' differs from the male parent, 'LE 06 0028', (unpatented) in that 'KLELE12472' has a mounding, medium compact habit, whereas 'LE 06 0028' has an upright, compact habit.

'KLELE12472' differs from the commercial variety 'Tech Hepdab' (U.S. Plant Pat. No. 21,049) in that 'KLELE12472' has a mounding, medium compact growth habit, whereas 'Tech Hepdab' has a half-hanging growth habit and is more vigorous.

We claim:

1. A new and distinct *Lobelia* plant named 'KLELE12472' as shown and described herein.

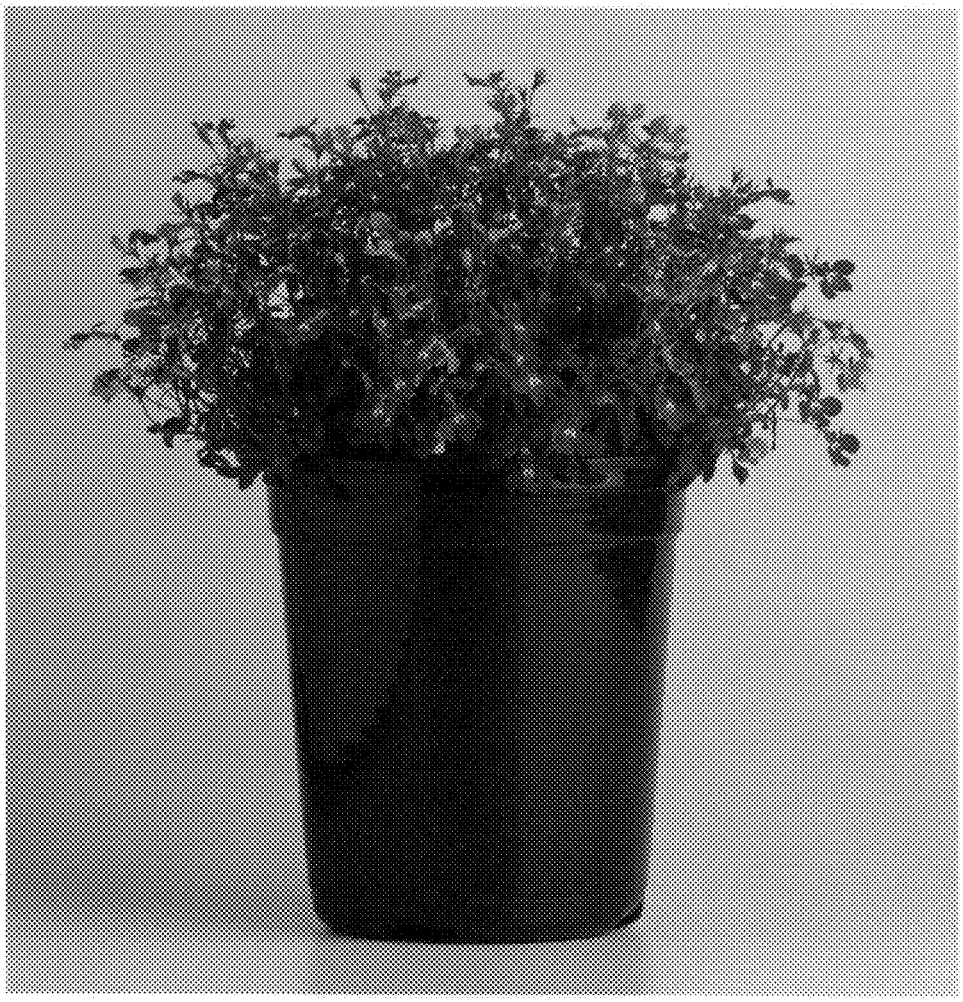

* * * * *